United States Patent [19]

Wiley

[11] 4,260,757
[45] Apr. 7, 1981

[54] POLY[di-1,2-(DIAZINYLIDENE)-ETHENE-1,2-DIOLS]

[76] Inventor: Richard H. Wiley, 8 Roosevelt Cir., Palo Alto, Calif. 94306

[21] Appl. No.: 58,389

[22] Filed: Jul. 18, 1979

[51] Int. Cl.³ .................... C07D 403/14; C07D 403/06
[52] U.S. Cl. .................................... 544/238; 544/296; 544/357; 544/225; 423/DIG. 4; 423/68; 423/11
[58] Field of Search ........................ 544/238, 296, 357

[56] References Cited
PUBLICATIONS

Heinisch et al., Chem. Abs. 85, 63016k (1976).
Rutner et al., Chem. Abs. 59, 8741g (1963).
Brederich et al., Chem. Abs. 62, 6482–6483 (1964).

*Primary Examiner*—Mark L. Berch

[57] ABSTRACT

Poly[di-1,2-(diazinylidene)-ethene-1,2-diols] having the structure:

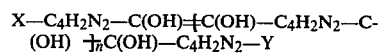

in which the $C_4H_2N_2$ group is a diazinylidene diradical having each C(OH) group adjacent (ortho) to one but not two ring nitrogen atoms and not adjacent (ortho) to each other; X and Y are terminal formyl (CHO) groups or groups derived from them by oxidation; and n has a value of zero to seven—are prepared by a cyanide ion catalyzed condensation of pyrazine-2,5-dicarboxaldehyde, pyridazine-3,6-dicarboxaldehyde; or pyrimidine-4,6-dicarboxaldehyde as the only aldehydes which provide the requisite structures. The polymers form complexes with metal ions including manganese, which is insoluble, and vanadium, which is soluble.

1 Claim, No Drawings

POLY[DI-1,2-(DIAZINYLIDENE)-ETHENE-1,2-DIOLS]

BACKGROUND OF THE INVENTION

There is no known carbon chain polymeric structure which embodies the structural features of 1,2-(2'-pyridyl)-ethene-1,2-diol nor is there any known process for obtaining polymers having such structures. The 1,2-(2-pyridyl)-ethene-1,2-diol is useful for its capability to complex various metal ions including specifically molybdenum.

SUMMARY OF THE INVENTION

Poly [di-1,2-(diazinylidene)-ethene-1,2-diols] having the structure:

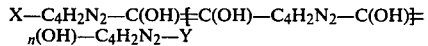

in which the $C_4H_2N_2$ group is a diazinylidene diradical having each C(OH) group adjacent (ortho) to one but not two ring nitrogens and not ortho to each other; the X and Y terminal groups are formyl (CHO) or groups derived from them by oxidation; and n has a value of zero to seven. These polymers are prepared by a cyanide ion catalyzed poly condensation of the corresponding dialdehydes: pyridazine-3,6-dialdehyde; pyrimidine-4,6-dialdehyde; or pyrazine-2,5-dialdehyde—the only reactants having the specified diazinylidene structure. The polymers have continuous carbon chains. Their formation could not have been predicted from the known reactions of the pyridine aldehydes. The products are useful as metal complexing agents in the separation of and refining of metals. A previously undescribed technique for the isolation of the aldehydes, including the previously unknown pyridazine-3,6-dialdehyde, is described.

DESCRIPTION OF THE INVENTION

The diazine dialdehydes used as monomers for their cyanide ion catalyzed polycondensation to the subject diazinylidene-ethene-1,2-diols, although previously unknown in their isolated forms, are prepared from commercially available starting materials by previously described reactions used for the synthesis of dialdehydes. These involve conversion of the corresponding dimethyl compounds; i.e., 3,6-dimethylpyridazine (from hexane-2,5-dione); 4,6-dimethyl-pyrimidine (commercially available); 2,5-dimethylpyrazine (commercially available), by standard techniques to these aldehydes. These include vapor phase air, selenium dioxide, manganese dioxide, and halogenation-hydrolysis oxidation. The aldehydes are also available by oxidation of the corresponding dimethanols with manganese dioxide. The dimethanols are available by lithium aluminum hydride reductions of the diacids or their esters. The dialdehydes are also available by the ozonolysis of the distyryl compounds and the nitrone hydrolysis reaction. The ozonolysis, nitrone hydrolysis, and the methanol oxidation are preferred for bench scale preparation. The solubility of these dialdehydes is similar to that of other dialdehydes. They form hydrates, are water soluble, and can be purified and used in water solution. They are unstable in light, heat, and air.

The cyanide ion catalyzed polycondensation of the diazine dialdehydes takes place in aqueous alkaline solution at ambient or slightly elevated temperatures; i.e., at 20°–100° C. A 5–20% solution of cyanide ion in ethanol or water or aqueous alcohol is added to a 5–75% solution of the dialdehyde in water or alcohol. The solution is allowed to react, after the initial immediate precipitation of product, at 20°–90° for up to several hours and the precipitated polymer collected. During this time both or either of the end groups of the polymer may undergo partial or complete spontaneous air oxidation from formyl (CHO) to carboxyl (COOH); bimolecular oxidation-reduction to (COOH/CH$_2$OH) groups; and decarboxylation (COOH to H).

The structures assigned to the polymers, on the basis of analytical data, are given in the following formulas:

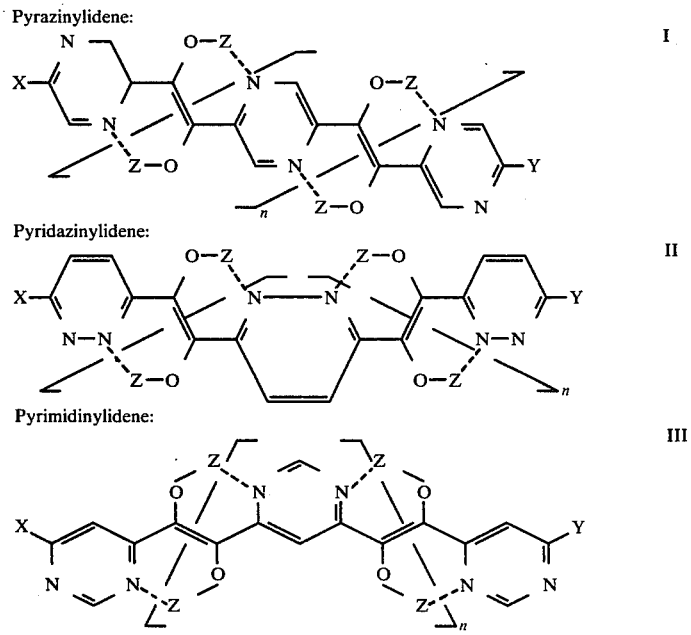

In these formulas X and Y are end groups whose structure is H, CHO, COOH(K); or CH₂OH in any combination as determined by the conditions of polymerization and isolation of the polymers. The value of n is from zero to seven (dimer to nonamer) with intermediate values and in mixtures as is characteristic of polymeric materials with averaged analytical data. As is characteristic of such structures, as noted for the dialdehydes themselves, they are also isolated as hydrated structures. Although illustrated with Z, the co-ordinated ion, as monovalent (i.e., hydrogen, potassium, etc.) this is not intended to suggest a limitation on the scope of the structural capability of the products of the invention. Co-ordination of ions of other valency; i.e., divalent (calcium, copper, mercury, etc.) and tri-or poly-valent (iron, manganese, palladium, etc.) is included. Further it is noted that the highly ordered, three dimensional structures of the polymers is not adequately illustrated by the two dimensional drawings of the formulas. The pyrazine and pyridazine structures are highly linear and crystalline; the pyrimidine is helically ordered. Such regular features derive from these three specific aldehydes as does also the characteristic juxtaposition of the enolic hydrogen (or other cation) and ring nitrogen to give a six membered chelate ring from both nitrogen atoms of each diazine ring as part of the regular polymeric structure. A unique result of this is that the products are soluble in acid as zwitterions and in base as anions.

The value of n, in the formulas, determines the molecular weight of the polymers and is itself determined by (1) the relative amounts of monoaldehydes which act as terminating groups and by (2) the conditions governing the condensation reaction. The relative amount of monoaldehyde is determined by the extent of oxidation of formyl to carboxyl groups, followed to some extent by loss of carbon dioxide to hydrogen on the ring, and the oxidation is determined by the presence of the requisite atmospheric oxygen, the amount of base catalyzed disproportionation of formyl to carboxyl and hydroxymethyl, and, in the oxidative preparative procedures, the amount of overoxidation by the oxidizing agent. The extent of the condensation is determined by the conditions used in the polymerization reaction; time, temperature, concentration of reactants and catalyst, pH, and conditions of mixing. Suitable control of these factors is achieved by definition, as given in the examples, of operable conditions of pH, concentration, time, temperature, exclusion of air, and stabilization with bisulfite.

The polymeric products of this invention are isolated as hydrates. Carboxylic acid (mono and poly) of the diazine series commonly form such hydrates as do also aldehydes, such as glyoxal and pyruvic aldehyde) having strong electron attracting substituents. The water may be combined as part of the crystal structure or as adducts at the carbonyl group or both. In either case attempts to remove the water are tedious and often required conditions destructive of the material. It is not taken as an indication of lack of purity or definition of structure and controlled conditions, as defined herein are required for non-destructive physical processing (recrystallization, isolation, storage) and chemical characterization of such hydrates.

The invention is described in further detail in the following examples.

EXAMPLE 1

A solution of pyrazine-2,5-dicarboxaldehyde in water is prepared by ozonolysis of 2,5-distyrylpyrazine in methanol. The ozonide is decomposed with aqueous bisulfite and the reaction mixture evaporated under vacuum at 30°. The residual aqueous solution of the dialdehyde is purified by extraction with ether—first while acidic, then while basic. From 2 g. of starting material there is obtained 15 ml of asolution of the dialdehyde (theory 0.96 g.). The pH isadjusted to pH 10–11 and 5 ml. of 2% aqueous potassium cyanide is added with cooling and stirring to dissipate the heat of reaction. There is an instantaneous formation of a red-brown precipitate turning black. Up to this point all operations have been conducted under an inert atmosphere and below 30°. The reaction mixture is heated 5 minutes on a steam bath. The pH is adjusted to 6.5. The product is collected as a red-brown solid and is dried in vacuum at 55° to give 0.3 g. of a black solid, soluble in alkali to give a deep maroon solution and soluble in acid. Anal. Calcd. for the nonamer (Formula I, n=7, X and Y=COOK) as its dodecahydrate: $C_{54}H_{33}N_{18}O_{20}K_3.12H_2O$: C, 40.80; H, 3.27; N, 15.87. Found: C, 41.16; H, 3.26; N, 15.78. Acid-base titration establishes the isoelectric point at pH 6.5. In acid, K of the formula is replaced by H.

EXAMPLE 2

Example 1 is repeated using 3,6-distyrylpyridazine. The polymerization is run for two hours at room temperature with one ml. of 10% potassium cyanide. There is obtained 0.2 g. of black solid pentamer (Formula II, n=3, X=COOH, Y=COOK) as the tetrahydrate with similar properties. Anal. Calcd. for $C_{30}H_{19}N_{10}O_{11}K.4H_2O$: C, 44.66; H, 3.34; N, 17.37. Found: C, 44.44; H, 3.61; N, 17.36.

EXAMPLE 3

Example 1 is repeated using 4,6-distyrylpyrimidine. The polymerization of the dialdehyde is run for 15 minutes on the steam bath. There is obtained 0.32 g. of black solid heptamer (Formula III, n=5, X=H, Y=COOK) as the tetrahydrate. Anal. Calcd. for $C_{41}H_{35}N_{14}O_{18}K.4H_2O$: C, 47.21; H, 3.36; N, 18.84. Found C, 47.00; H, 3.54; N, 18.71. The properties are those given for the polymer of example 1.

EXAMPLE 4

Example 2 is repeated. The ether extracted, aqueous solution of the pyridazine-3,6-dialdehyde is extracted with dichloromethane repeatedly and the extracts evaporated to leave a residue of the dialdehyde. This semisolid residue is dissolved in 1 ml of water and 1 ml of 10% potassium cyanide is added with cooling. The precipitated solid is collected and dried to give the heptamer as the tripotassium salt tetrahydrate (Formula II, n=7, X=H, Y=H). Anal. Calcd. for $C_{40}H_{25}N_{14}O_{12}K_3.4H_2O$: C, 44.36; H, 3.05; N, 18.11. Found: C, 44.61; H, 3.31; N, 18.18. The polymer is soluble in base to give a deep maroon solution.

EXAMPLE 5

Example 4 is repeated. The residual solid from the extraction is vacuum sublimed to give bright yellow crystals of pyridazine-3,6-dicarboxaldehyde, mp. 106–8. The crystals are hydroscopic and soluble in water. Anal. Calcd. for $C_6H_4N_2O_2.0.11H_2O$: C, 52.94; H, 2.94; N, 20.58. Found: C, 52.29; H, 3.24; N, 20.23. The yellow crystals can be recrystallized from ethyl acetate. The crystals decompose slowly to a green-black solid on standing at room temperature under nitrogen and protect d from light; very quickly if not protected. A 0.6 g. sample dissolved in 1 ml of water and polymerized with 0.1 ml of 10% aqueous potassium cyanide gave the polymer as a black solid soluble in base to give a deep maroon solution and soluble in acid.

EXAMPLE 6

The use of the polymers in the selective precipitation of metal ions is shown by adding solutions of the metal ion to a solution of the polymer in dilute base. A solution of the polymer prepared as in example 1 is diluted to a dark, but transparent maroon color. Addition of dil. hydrochloric acid will lighten this color but form no precipitate. Addition of a dilute solution of ferric chloride gives an immediate black coarse predipitate and complete decolorization of the solution. Addition of a dilute solution of a vanadium salt gives a dark green or blue solution from which no precipitate forms even after long standing. Other ions which cause an immediate precipitation and decolorization are calcium, silver, cerium, and manganese. The solubilization of vanadium in the presence of manganese or uranium is useful in the metallurgy and refining of carnotite and sea nodules. The uranium salt is insoluble.

EXAMPLE 7

One gram of 3,6-dimethylpyridazine is refluxed in 200 ml. of chloroform with 12 g. of active manganese dioxide for 3 days. The mixture is filtered and the filtrate evaporated. The residue is dissolved in 2 ml. of water and to this solution is added 1 ml. of 10% potassium cyanide. There is an immediate formation of a red-brown turning black precipitate of the pyridazinylidene ethenediol polymer.

EXAMPLE 8

Example 7 is repeated using 2 g. of selenium dioxide in 50 ml. of dry ethyl acetate at room temperature for 15 hours. The addition of aqueous potassium cyanide to the filtrate gives an immediate predipitate of the red-brown pyridazinylidene ethene diol polymer.

EXAMPLE 9

One gram of the nitrone prepared from 2,5-dimethylpyrazine and nitroso-N,N-dimethylaniline is dissolved in dilute acid. After 15 minutes at room temperature, the solutions is made alkaline with ethanolic potassium hydroxide and to it is added 1 ml. of 10% ethanolic potassium cyanide to precipitate the red-brown dipyrazinylidene ethene diol polymer. The polymer is purified by washing with alcohol and then with ether.

EXAMPLE 10

Example 1 is repeated using dimethyl sulfide in place of bisulfite. With 3,6-distyrylpyridazine, the product is the dimeric acid (Formula I, $n=0$, $X=Y=COOH$) as its hydrate. Anal. Calcd. for $C_{12}H_8N_4O_6 \cdot H_2O$: C, 44.72; H, 3.11; N, 17.4. Found: C, 44.93; H, 3.19; N, 17.45.

EXAMPLE 11

Example 10 is repeated using 2,5-distyrylpyrazine. The product is the dipotassium salt of trimer (Formula II, $n=1$, $X=Y=COOK$) as its tetrahydrate. Anal. Calcd. for $C_{18}H_{10}N_6O_8K_2 \cdot 4H_2O$: C, 36.73; H, 3.06; N, 14.28. Found: C, 36.66; H, 2.91; N, 14.38.

What is claimed is:

1. Poly[di-1,2-(diazinylidene)-ethene-1,2-diols] having the structures:

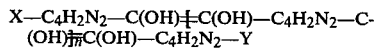

in which the $C_4H_2N_2$ group is a diazinylidene diradical having each C(OH) group adjacent (ortho) to one but not two ring nitrogen atoms and not adjacent (ortho) to each other; the X and Y terminal groups are H, COOH, and COOK; and n has a value of one to seven.

* * * * *